United States Patent [19]
Harris

[11] 3,985,140
[45] Oct. 12, 1976

[54] DUAL PRESSURE VALVE FOR USE IN VENTRICULAR SHUNT SYSTEM

[75] Inventor: Donald L. Harris, Miami, Fla.

[73] Assignee: Cordis Corporation, Miami, Fla.

[22] Filed: June 30, 1975

[21] Appl. No.: 591,657

[52] U.S. Cl. ............................ 128/350 V; 128/274; 251/342
[51] Int. Cl.² ...................................... A61M 27/00
[58] Field of Search ............ 128/350 R, 350 V, 274; 251/342; 137/599, 269.5

[56] References Cited
UNITED STATES PATENTS

| | | |
|---|---|---|
| 3,288,142 | 11/1966 | Hakim ............................ 128/350 V |
| 3,819,151 | 6/1974 | Kish ................................... 251/342 |
| 3,827,439 | 8/1974 | Schulte ........................... 128/350 V |
| 3,889,687 | 6/1975 | Harris et al. ..................... 128/350 V |

Primary Examiner—Dalton L. Truluck
Attorney, Agent, or Firm—Kenway & Jenney

[57] ABSTRACT

The dual pressure valve assembly disclosed herein is adapted for use in a ventricular shunt system and comprises a housing enclosing a pair of one-way, pressure biased valves. One of the valves is fixed in place and the second valve is adapted for shifting between an on-line position, in which the valves are in series and their bias pressures combined, and an off-line position in which the second valve is bypassed.

5 Claims, 5 Drawing Figures

DUAL PRESSURE VALVE FOR USE IN VENTRICULAR SHUNT SYSTEM

BACKGROUND OF THE INVENTION

This invention relates to ventricular shunt systems, and more particularly to a dual pressure shunt valve assembly which may be operated to maintain either one of two cerebro spinal fluid pressures in the ventricles of a patient's brain.

The treatment of hydrocephalus frequently involves the implantation of a ventricular shunt for draining excess cerebral spinal fluid (CSF) from the ventricle in the brain. The shunt generally consists of a cerebral catheter inserted through the brain tissue into the ventricle and connected through a one-way valve system to drain into the jugular vein or other resevoir in the body. The shunt provides for removal of excess CSF from the ventricle and consequent reduction in its size. Control over the drainage is provided by the one-way valve, which is normally biased to operate at a fixed back pressure at normal flow.

Although hydrocephalus is frequently associated with an abnormally high CSF pressure, there are numerous cases where hydrocephalus is associated with the CSF at normal pressure, see Ojemann, Robert G., Normal Pressure Hydrocephalus, *Clinical Neurosurgery*, Vol. 18, pp. 337–370, 1971.

An analysis of the hydromechanics involved in normal pressure hydrocephalus syndrome leads to the conclusion that the effective expansion force on the ventricles is not dependent on the CSF pressure alone, but is the product of the CSF pressure and ventricular area. In other words, in the presence of ventricular enlargement the pressure may be "normal." Thus, in normal pressure hydrocephalus the ventricle remains enlarged, because the area subjected to the pressure of the CSF is larger than normal and hence the total force on the brain tissue, the product of the pressure times the area, is excessive. (See, S. Hakim and R. D. Adams., The special clinical problem of symptomatic hydrocephalus with normal cerebrospinal fluid pressure: Observations on cerebrospinal fluid hydrodynamics. J. Neural. Sci., Vol. 2 pp. 307–327, 1965).

In addition to the forces developed by the CSF pressure, the brain tissue is subjected to a counterforce developed by the venous pressure within the intraparenchymatous system, within the brain tissue itself. Whereas CSF pressure tends to enlarge the ventricles, the venous pressure tends to reduce their size. These two forces are normally in balance so that the ventricular size relationship does not increase nor decrease, but remains constant through life.

Accordingly, the aim in treating hydrocephalus by shunting procedures in not merely to arrest the condition, but to restore, as much as possible, normal ventricular size. Once hydrocephalus has developed, this restoration is accomplished by reversing the imbalance of the two forces acting on the brain parenchyma. The CSF pressure must be reduced to offset the increased force developed by virtue of the enlarged area of the ventricles. Then the forces developed within the venous system can cause the compressed brain tissue to "spring back" against the lower CSF force, and the venous bed will regain its lost volume and free flow. This way, the brain metabolism becomes normal and the tissue recuperates.

In treating hydrocephalus, a reduced CSF pressure is established by a shunt which includes a oneway valve having an operating pressure equal to the desired CSF pressure. With the shunt in place the CSF pressure remains at a maximum level determined by the implanted valve, and drainage of CSF from the ventricles continues as long as CSF pressure is not less than the operating pressure of the valve. Since the correction of normal pressure hydrocephalus requires the implantation of a valve having a lower than normal operating pressure, e.g. approximately 30–40 mm $H_2O$, depending on the size of the ventricles. The CSF pressure remains lower than normal as the ventricles decrease in size. On the other hand, since the venous pressure remains at normal levels, the force imbalance is reversed. The venous system force becomes greater than the CSF system force because of the progressively smaller ventricular area and lowered CSF pressure. Accordingly, once the ventricle is again normal size, the intraventricular CSF pressure must be broughtback to normal levels. Otherwise, there is not enough force within the ventricles to keep them normally expanded.

If lower than normal CSF pressure is maintained, overcorrection of hydrocephalus may cause undesirable pathological consequences, such as cerebral edema, "slit ventricles" and microcephaly. In other cases, complications such as subdural hygromas, hematomas, and overlapping of the skull bones are known to occur.

In brief, the problem is corrected by maintaining the intraventricular CSF at a reduced pressure until such time that the ventricular volume is reduced to normal size. At this point, the valve provided for the initial drainage should be replaced with one having a closing pressure equivalent to a normal CSF pressure, 125–150 mm $H_2O$, or higher to act only as a safety valve if the bodies own absorptive system is functioning partially or totally.

A second reason for exchanging the initially installed reduced pressure valve for a high pressure valve at a later time stems from the theory that a high pressure valve may tend to coax the body's normal drainage systems to function, hence preventing the patient from becoming valve dependent.

A third reason to exchange pressures is the theory that, during the initial healing stage, a higher pressure should be maintained to prevent the possibility of hematomas or hygromas developing at the intrusion site and to lower the pressure a few days or hours later to reduce the ventricle size.

Accordingly, it is an object of the present invention to provide a dual pressure valve assembly for use in series with a ventricular catheter and an implantable drain system such as those described, which can be easily manipulated so as to change from a low pressure mode to a higher, closer-to-normal, pressure mode and thereby eliminates the necessity of replacing the shunt system. Preferably, the adjustment should be accomplished quickly, easily, and effectively by a simple manual procedure performed without surgery. Other objects of the invention are to provide a ventricular shunt system which is dependable, simple, inexpensive to manufacture, useful in treating both high and normal CSF pressure hydrocephalus, and capable of being shifted as necessary, at various times in the hydrocephalus treatment period, in a rapid and safe manner, the position of the shiftable valve being easily detected by feel or normal x-ray techniques.

SUMMARY OF THE INVENTION

In general, the invention features a dual pressure shunt valve used in series with a ventricular catheter and an implantable tube system. The shunt valve comprises: a housing; disposed within the housing, a first one-way valve having a threshold operating pressure for maintaining a low level of CSF pressure within the ventricles of the patient, and; also disposed within the housing, a second one-way valve, likewise having a threshold operating pressure for maintaining CSF pressure within the ventricles. The second valve is adapted for shifting between an on-line position and an off-line position. In the on-line position, the first and second valves are in series and CSF pressure is maintained at a relatively high level resulting from the sum of the respective operating pressures of the valves. In the off-line position, the second valve is bypassed and the patient's CSF pressure is maintained at a low level, i.e., that resulting from the operating pressure of the first valve alone. In preferred embodiments, the housing comprises a hollow, elastomeric transversely enlarged portion of the shunt system defining an on-line nesting position and an off-line nesting position. The second valve is frictionally held in either nesting position but may be shifted, by application of external force on the elastomeric enlarged portion, to the on-line nesting position, and thereafter frictionally held in place. The sideways motion is designed to require intentional manipulation that minimizes accidental pressure mode changes. The valve and nesting positions are radiopaque for x-ray visualization of the pressure mode set.

Other advantages and features of the invention will be apparent from the detailed description of a preferred embodiment and the following drawings wherein.

DESCRIPTION OF THE PREFERRED EMBODIMENT

Figure 1:
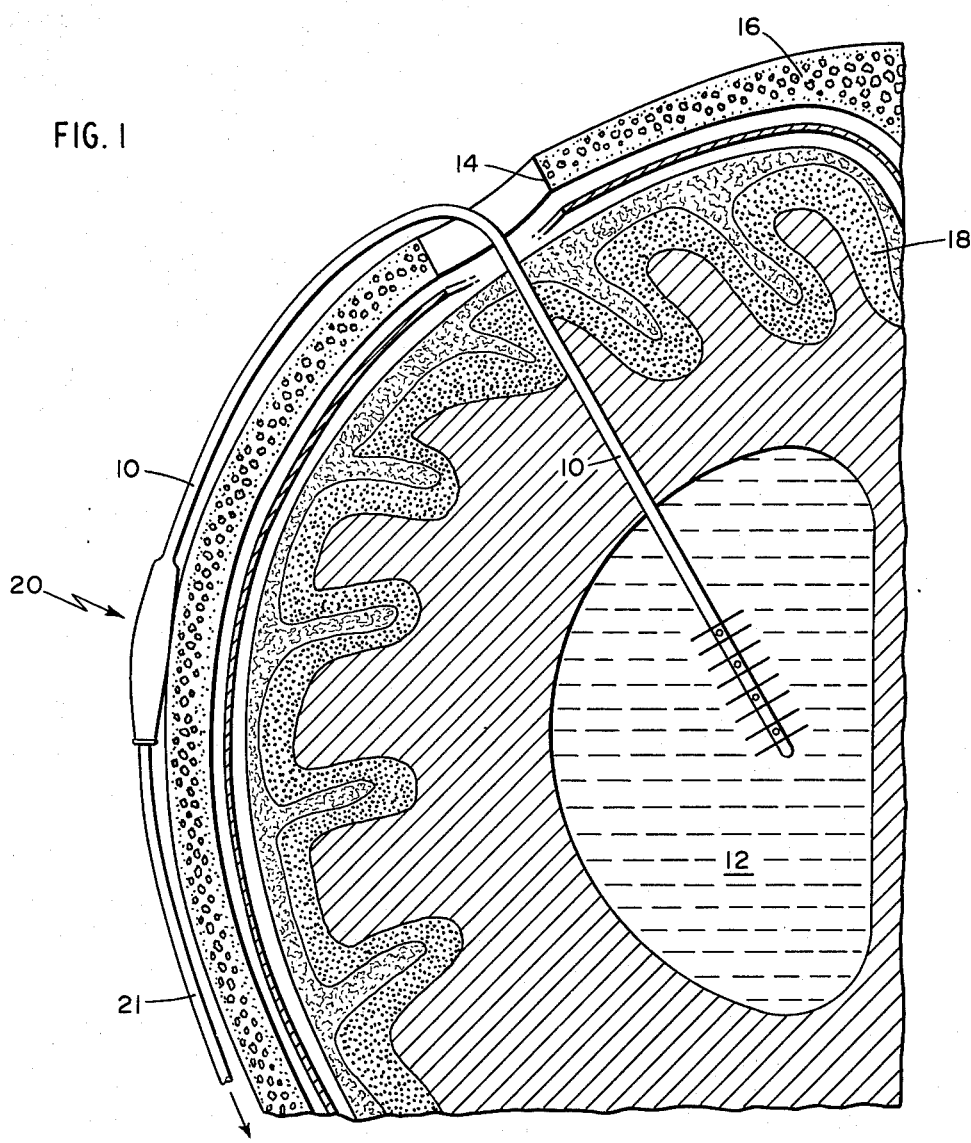
FIG. 1 is a schematic illustration showing the valve system in its physiological environment.

The implantation of the ventricular shunt is illustrated in FIG. 1. The ventricular catheter 10 is inserted through a burr hole 14 is the skull 16 and through the brain tissue 18, into the ventricles 12. The catheter 10 is connected to a drainage catheter or tube 21 through the novel shunt valve of the invention, generally designated at 20. Tube 21 will normally lead to the right atrium, the pertoneal cavity, or some other suitable reservoir.

Figure 2:
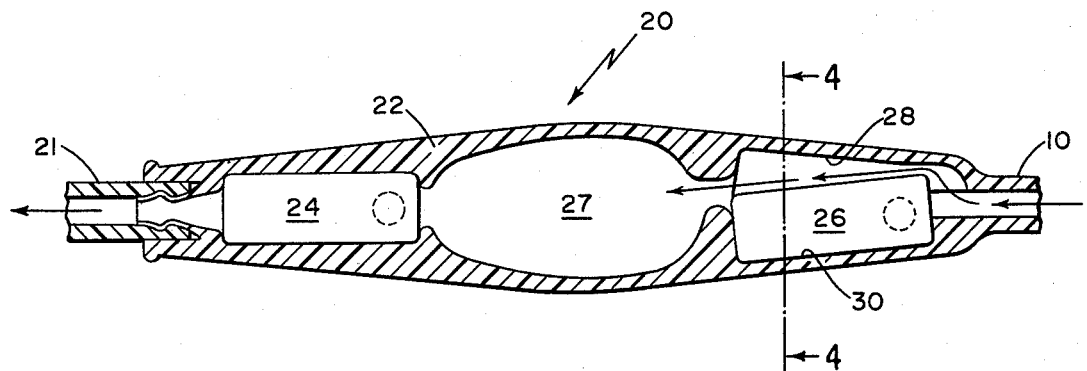
FIG. 2 is a partial cross-section of an embodiment of the valve assembly of the invention, with the shiftable valve in the off-line position.

Dual pressure shunt valve assembly 20, as seen in FIG. 2, comprises a housing 22 which encloses a first one-way valve 24, and a second, shiftably mounted one-way valve 26. A cavity 27 is provided between the two valves. Preferably, the housing is formed from the same material from which the catheters 10 and 21 were formed, e.g. radiopaque silicone rubber, but, in any case, should be made of an elastomeric, non-toxic, radiopaque material, preferably capable of high-temperature sterilization.

Figure 4:
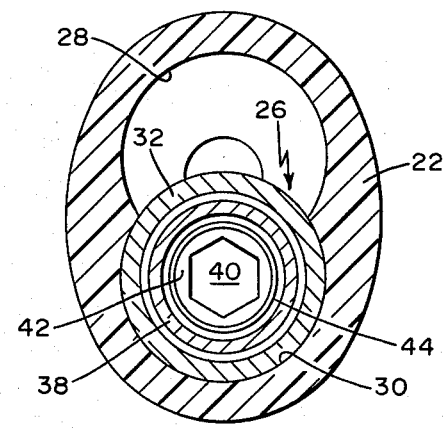
FIG. 4 is an enlarged cross-sectional view taken substantially on the line 4—4 of FIG. 2.

As may be seen in FIGS. 2 and 4, the portion of the housing 22 which contains the valve 26 is shaped to define two distinct valve nesting positions 28, 30, one of which is on-line and the other of which is off-line. In normal operation, the valve 26 will be frictionally retained in one or the other of these nesting positions.

Figure 5:
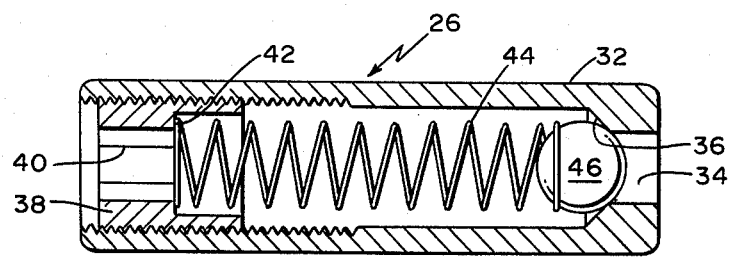
FIG. 5 is an enlarged cross-sectional view of a valve as might be used in the invention.

The valves 24 and 26 are of similar design and are described in more detail in Applicant's U.S. application Ser. No. 438,217 now U.S. Pat. No. 3,889,687. As seen in FIG. 5, each of the valves is formed from a hollow elongated cylinder 32 having a fluid entrance passage 34 which leads to a conical shaped surface 36. The downstream end of cylinder 32 is threaded to receive insert 38, which defines a hexagonal fluid exit passage 40 and an annular shoulder 42. A coil spring 44 rests against shoulder 42 and provides resilient tension on a ball 46. The conical surface 36 is polished to a mirror-like finish, and the ball 46 is sized to sealingly engage it. The force that spring 44 exerts on the ball determines the threshold operating pressure of the valve; this force may be varied by rotating insert 38 with a tool before the valve is placed in housing 22, thus varying the distance between the shoulder 42 and ball 46 and changing the pressure of the spring.

Figure 3:
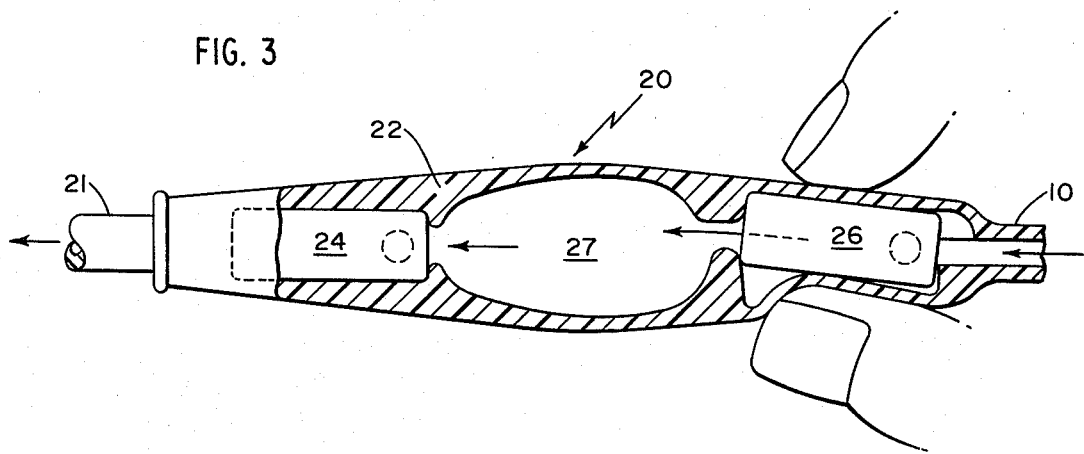
FIG. 3 is a partial cross-section identical to that of FIG. 2 except that the shiftable valve is shown being shifted to the on-line position.

In operation, the ventricular catheter 10 is inserted through the burr hole 14 of the skull by well-known surgical techniques, and the drainage catheter 21 is inserted into, e.g., the patient's jugular vein. As in generally done with ventricular shunts, the entire drainage assembly is ultimately covered and held in place by the scalp (not shown). After the surgeon installs the system, during the first stages of the treatment period, the dual pressure shunt valve should be in the configuration shown in FIG. 2. In this mode, valve 26 is bypassed so that it does not contribute to the back pressure. The valve 24 both acts as a check valve to prevent backflow of CSF fluid, and maintains a threshold operating pressure dictated by the force exerted by spring 44 on ball 46. A pressure of 30–40 mm $H_2O$ has been found effective to induce shrinkage of most ventricles. The dual pressure shunt valve assembly remains in this mode until the physician determines that the patient's ventricle is normally sized. At this time, if the reduced operating pressure is maintained, overcorrection of hydrocephalus may result along with its aforementioned undersirable pathological consequences. To prevent this overcorrection, valve 26 is simply manually shifted to its on-line nesting position 28, as shown in FIG. 3. Valve 26 will differ from valve 24 in that the compression of spring 44 should be such that the threshold operating pressure is in the vicinity of 100–120 mm $H_2O$. When the valves are shifted to this on-line or series position, as described, the total threshold operating pressure of the valve assembly will be in the vicinity of 130–160 mm $H_2O$, i.e., close to normal levels. (When the normal absorptive system is functioning at normal pressure, i.e., normal pressure hydrocephalus, the high pressure mode of the valve may be set higher than normal to act as a safety valve only, i.e., 180–210 mm $H_2O$.) If, for any reason, it is desirable to again reduce CSF pressure, valve 26 may be simply shifted to its off-line position.

While the above describes and illustrates a preferred embodiment of the invention, it should be understood that the invention is not restricted solely to the described embodiment but covers all modifications which would be apparent to those skilled in the art and which would fall within the scope and spirit of the invention as defined in the following claims.

What is claimed is:

1. A dual pressure shunt valve assembly for use in series with a ventricular catheter and an implantable drainage system employed in venting CSF from a patient's ventricles, said valve assembly comprising:
a housing;
disposed within said housing, a first one-way valve having a threshold operating pressure appropriate for maintaining a relatively low level of CSF pressure within the ventricles; and
disposed within said housing, a second one-way valve having a respective threshold operating pressure, means defining a pair of separate second valve positions, and retention means for maintaining said second valve in a selected one of said positions until said second valve is shifted, said pair of positions comprising an on-line position, wherein said first and second valves are in series and the patient's CSF pressure is maintained at a relatively high level resulting from the combined effect of the operating pressures of said valves, and an off-line position, wherein said second valve is bypassed and the patient's CSF pressure is maintained at the relatively low level resulting from the operating pressure of said first valve alone, whereby said second valve may be shifted between said positions to change the level of CSF pressure to be maintained within the ventricles.

2. A ventricular shunt system of the type including a ventricular catheter, an implantable drainage system for venting CSF from a patient's ventricles, and a one-way valve in series with said catheter and said drainage system, said valve having a threshold operating pressure for maintaining less than normal CSF pressure within the patient's ventricles, wherein the improvement comprises:
a second one-way valve disposed within said system in a housing defining a pair of separate valve positions, said positions comprising an off-line position, wherein CSF bypasses said second valve, and an on-line position, in series with said first valve, wherein CSF passes through both said first and second valves, said second valve having a threshold operating pressure for maintaining CSF pressure in the patient's ventricle, said housing further defining retention means for maintaining said second valve in a selected one of said positions until said second valve is shifted, whereby, when said valves are in series, the patient's ventricular CSF pressure is increased.

3. The improvement of claim 2 wherein said second valve is frictionally held within a hollow, elastomeric, transversely enlarged portion of said shunt system having an interior wall defining both an on-line valve nesting position and off-line valve nesting position, said nesting positions together comprising said retention means, whereby said second valve is frictionally held in said off-line nesting position until shifted, by the application of external force on said elastomeric portion, to said on-line nesting position, and thereafter is frictionally held in place.

4. A dual pressure shunt valve assembly for use in series with a ventricular catheter and an implantable drainage system employed in venting CSF from a patient's ventricles, said valve assembly comprising:
a hollow, elastomeric housing having an interior wall defining both an on-line valve nesting position and an off-line valve nesting position;
disposed within said housing, a first one-way valve having a threshold operating pressure appropriate for maintaining a relatively low level of CSF pressure within the ventricle, and;
disposed within said housing, a second one-way valve having a respective threshold operating pressure, said second valve being adapted for shifting between said on-line valve nesting position, wherein said first and second valves are in series and the patient's CSF pressure is maintained at a relatively high level resulting from the combined effect of the operating pressures of said valves, and said off-line valve nesting position, wherein said second valve is bypassed and the patient's CSF pressure is maintained at the relatively low level resulting from the operating pressure of said first valve alone, whereby, said second valve is frictionally held in one of said nesting positions until shifted, by the application of external force on said housing, to the other nesting position, and thereafter is frictionally held in place.

5. A ventricular shunt system of the type including a ventricular catheter, an implantable drainage system for venting CSF from a patient's ventricles, and a one-way valve in series with said catheter and said drainage system, said valve having a threshold operating pressure for maintaining less than normal CSF pressure within the patient's ventricles, wherein the improvement comprises:
a second one-way valve disposed within a hollow, elastomeric, transversely enlarged portion of said shunt system having an interior wall defining a pair of valve nesting positions, said nesting positions together defining mounting means for shifting said second valve between an off-line position, wherein said valve is frictionally held in place and CSF bypasses said second valve, to an on-line position, in series with said first valve, wherein said second valve is frictionally held in place and CSF passes through both said first and second valves, said second valve having a threshold operating pressure for maintaining CSF pressure in the patient's ventricle, whereby, when said valves are in series, the patient's ventricular pressure is increased.

* * * * *